US00PP33679P2

(12) United States Plant Patent
van Sambeek

(10) Patent No.: US PP33,679 P2
(45) Date of Patent: Nov. 23, 2021

(54) ***PHLOX* PLANT NAMED 'DOPHLOFLAPROPIPO'**

(50) Latin Name: *Phlox paniculata*
Varietal Denomination: Dophloflapropipo

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/203,634

(22) Filed: Mar. 16, 2021

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
CPC ... A01H 5/02; A01H 5/00; A01H 6/70; A01H 6/36
See application file for complete search history.

*Primary Examiner* — June Hwu
(74) *Attorney, Agent, or Firm* — C. Anne Whealy

(57) ABSTRACT

A new and distinct cultivar of *Phlox* plant named 'Dophloflapropipo', characterized by its upright and uniform plant habit; vigorous growth habit and rapid growth rate; relatively freely branching habit; freely flowering habit; dense inflorescences with reddish purple-colored flowers with darker reddish purple-colored centers; and good garden performance.

1 Drawing Sheet

Botanical designation: *Phlox paniculata.*
Cultivar denomination: 'DOPHLOFLAPROPIPO'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Jan. 13, 2021, application number 2021/0129. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phlox* plant, botanically known as *Phlox paniculata* and hereinafter referred to by the name 'Dophloflapropipo'.

The new *Phlox* plant is a product of a planned breeding program conducted by the Inventor in Aalsmeer, The Netherlands. The objective of the breeding program was to create new early and freely-flowering *Phlox* plants with attractive flower color.

The new *Phlox* plant originated from a cross-pollination made by the Inventor in July, 2013 in Aalsmeer, The Netherlands, of a proprietary selection of *Phlox paniculata* identified as code number PA06-000055-001, not patented, as the female, or seed, parent with a proprietary selection of *Phlox paniculata* identified as code number PA-0049, not patented, as the male, or pollen, parent. The new *Phlox* plant was discovered and selected by the Inventor as a single flowering plant from within the progeny of the stated cross-pollination in a controlled environment in Aalsmeer, The Netherlands in July, 2014.

Asexual reproduction of the new *Phlox* plant by vegetative cuttings in a controlled environment in Aalsmeer, The Netherlands since August, 2014 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dophloflapropipo'. These characteristics in combination distinguish 'Dophloflapropipo' as a new and distinct *Phlox* plant:

1. Upright and uniform plant habit.
2. Vigorous growth habit and rapid growth rate.
3. Relatively freely branching habit.
4. Freely flowering habit.
5. Dense inflorescences with reddish purple-colored flowers with darker reddish purple-colored centers.
6. Good garden performance.

Plants of the new *Phlox* differ from plants of the female parent selection in flower color as plants of the new *Phlox* have lighter reddish purple-colored flowers than plants of the female parent selection. In addition, plants of the new

*Phlox* have non-variegated leaves whereas plants of the female parent selection have variegated leaves.

Plants of the new *Phlox* differ primarily from plants of the male parent selection in plant habit as plants of the new *Phlox* are more uniform than plants of the male parent selection.

Plants of the new *Phlox* can be compared to plants of *Phlox paniculata* 'Ditosdre', disclosed in U.S. Plant Pat. No. 20,597. In side-by-side comparisons, plants of the new *Phlox* and 'Ditosdre' differ in the following characteristics:

1. Plants of the new *Phlox* are more freely branching than plants of 'Ditosdre'.
2. Plants of the new *Phlox* have smaller flowers than plants of 'Ditosdre'.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph comprises a top perspective view of typical flowering plant of 'Dophloflapropipo' grown in a container.

DETAILED BOTANICAL DESCRIPTION

The aforementioned photograph and following observations, measurements and values describe plants grown during the early summer in 17-cm containers initially in a glass-covered greenhouse and finished in an outdoor nursery in Aalsmeer, The Netherlands and under cultural practices typical of commercial *Phlox* production. During the production of the plants, day temperatures averaged 21° C. and night temperatures averaged 15° C. Plants were pinched one time one week after planting rooted young plants and were 32 weeks old when the photograph and the description were taken. In the following description, color references are made to The Royal Horticultural Society Colour Chart, Second Edition, except where general terms of ordinary dictionary significance are used.

Botanical classification: *Phlox paniculata* 'Dophloflapropipo'.

Parentage:

*Female, or seed, parent*.—Proprietary selection of *Phlox paniculata* identified as code number PA06-000055-001, not patented.

*Male, or pollen, parent*.—Proprietary selection of *Phlox paniculata* identified as code number PA-0049, not patented.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Thick, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright and uniform plant habit; vigorous growth habit and rapid growth rate.

*Plant height*.—About 32 cm.

*Plant width* (*spread*).—About 35 cm.

*Lateral branches*.—Branching habit: Relatively freely branching habit; about three primary branches each with about three secondary branches. Length: About 20 cm. Diameter: About 4 mm. Internode length: About 2.5 cm. Strength: Strong. Aspect: Upright to about 35° from vertical. Texture and luster: Smooth, glabrous; glossy. Color: Close to 143A; if woody, close to 199B.

Leaf description:

*Arrangement*.—Opposite, simple.

*Length*.—About 7.5 cm.

*Width*.—About 3.2 cm.

*Shape*.—Lanceolate.

*Apex*.—Acute.

*Base*.—Cuneate.

*Margin*.—Ciliate.

*Texture and luster, upper surface*.—Smooth, glabrous; towards the margins, rough; glossy.

*Texture and luster, lower surface*.—Smooth, glabrous; towards the margins, rough; matte.

*Venation pattern*.—Pinnate, reticulate.

*Color*.—Developing leaves, upper surface: Close to 137A. Developing leaves, lower surface: Close to 137C. Fully expanded leaves, upper surface: Close to 147A; venation, close to 147B. Fully expanded leaves, lower surface: Close to 147B; venation, close to 146D.

*Petioles*.—Length: About 3 mm. Diameter: About 3 mm. Strength: Moderately strong. Texture and luster, upper and lower surfaces: Smooth, glabrous; glossy. Color, upper surface: Close to 144A. Color, lower surface: Close to 146D.

Flower description:

*Flower type and flowering habit*.—Single rotate and salverform flowers arranged in compound terminal and lateral panicles; flowers face mostly upright to outwardly depending on position on inflorescence; freely flowering habit with about 36 flowers per inflorescence and about 780 flowers developing per plant during the flowering season.

*Fragrance*.—Slightly fragrant; sweet, pleasant.

*Natural flowering season*.—Plants begin flowering about 22 weeks after planting; plants flower during June and July in the garden in The Netherlands; flowers not persistent.

*Flower buds*.—Height: About 2 cm. Diameter: About 5 mm. Shape: Conical. Texture and luster: Smooth, glabrous; matte. Color: Close to 67B; at the base, close to 157D.

*Inflorescence height*.—About 10 cm.

*Inflorescence diameter*.—About 12 cm.

*Flower diameter*.—About 3 cm.

*Flower depth*.—About 2.7 cm.

*Flower throat diameter*.—About 5 mm.

*Flower tube length*.—About 2 cm.

*Flower diameter, proximally*.—About 3 mm.

*Petals*.—Quantity per flower: Typically five in a single whorl; petals fused at the base into a narrow tube. Lobe length: About 1.2 cm. Lobe width: About 1.5 cm. Lobe shape: Obovate. Lobe apex: Rounded. Lobe margin: Entire, not undulate. Lobe texture and luster, upper and lower surfaces: Smooth, glabrous; matte. Throat texture: Smooth, glabrous. Tube texture: Smooth, glabrous. Color: Lobe, when opening, upper surface: Close to 67A; towards the throat, close to 74A. Lobe, when opening, lower surface: Close to 67D. Lobe, fully opened, upper surface: Close to 67B; towards the throat, close to 74A; venation, similar to lamina; color becoming closer to 72C and towards the center, close to 74B, with development. Lobe, fully opened, lower surface: Close to 67D; venation, close to 67D; color becoming closer to 69A with development. Throat: Close to 67D; venation, close to 67D. Tube: Close to 67B; venation, close to 67B.

*Sepals*.—Quantity per flower: Typically five in a single whorl, fused towards the base; calyx, tubular. Length: About 7 mm. Width: About 1 mm. Shape: Subulate. Apex: Acuminate. Margin: Entire. Texture and luster, upper and lower surfaces: Smooth, glabrous; semi-glossy. Color: When opening, upper and lower surfaces: Close to 144A. Fully opened, upper and lower surfaces: Close to 144A.

*Peduncles*.—Length: About 2 cm. Diameter: About 2 mm. Strength: Moderately strong. Aspect: About 45° from lateral branch axis. Texture and luster: Smooth, glabrous; glossy. Color: Close to 143A.

*Pedicels*.—Length: About 5 mm. Diameter: About 1 mm. Strength: Moderately strong. Aspect: Up to 40° from peduncle axis. Texture and luster: Smooth, glabrous; glossy. Color: Close to 144A.

*Reproductive organs*.—Stamens: Quantity per flower: Typically five. Filament length: About 1.4 mm. Filament color: Close to 155A. Anther size: About 1 mm by 2 mm. Anther color: Close to 157A. Pollen amount: Moderate. Pollen color: Close to 155A. Pistils: Quantity per flower: One. Pistil length: About 1.7 cm. Stigma diameter: Less than 1 mm. Stigma shape: Three-parted. Stigma color: Close to 145A. Style length: About 1.2 cm. Style color: Close to 77B. Ovary color: Close to 143A.

*Seeds and fruits*.—To date, seed and fruit development have not been observed on plants of the new *Phlox*.

Garden performance: Plants of the new *Phlox* have been observed to have good garden performance and to tolerate rain, wind and temperatures ranging from about −37° C. to about 35° C.

Pathogen & pest resistance: To date, plants of the new *Phlox* have not been observed to be resistant to pathogens and pests common to *Phlox* plants.

It is claimed:

1. A new and distinct *Phlox* plant named 'Dophloflapropipo' as illustrated and described.

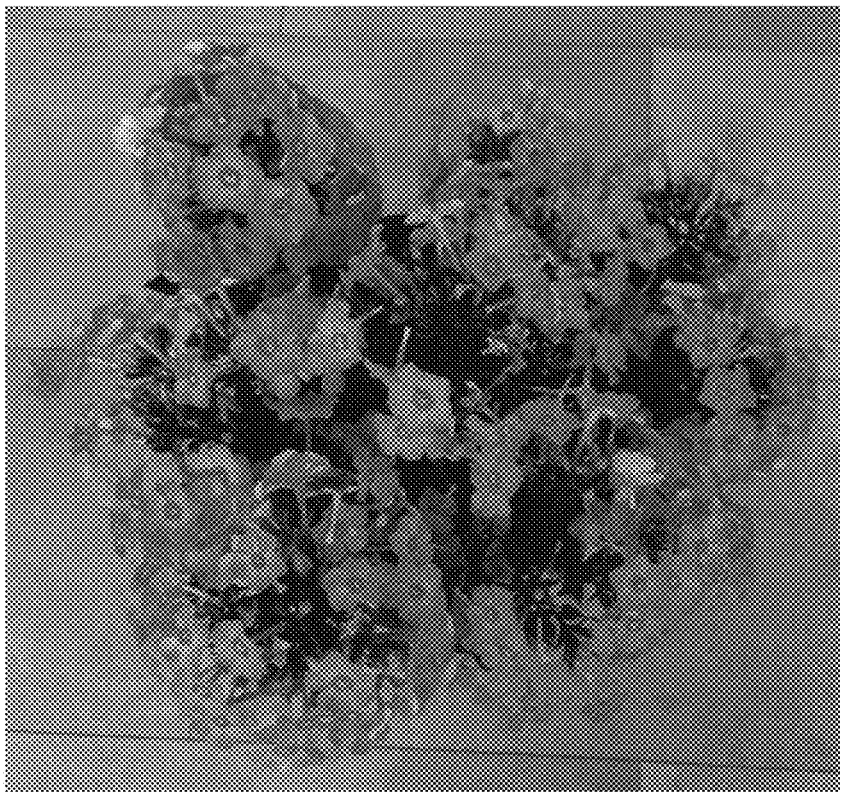

* * * * *